United States Patent
Keene et al.

(10) Patent No.: US 9,617,581 B2
(45) Date of Patent: Apr. 11, 2017

(54) METHODS FOR IN VIVO IDENTIFICATION OF ENDOGENOUS MRNA TARGETS OF MICRORNAS

(75) Inventors: Jack D. Keene, Durham, NC (US); Patrick J. Lager, Efland, NC (US)

(73) Assignee: Duke University, Durham, NC (US)

( * ) Notice: Subject to any disclaimer, the term of this patent is extended or adjusted under 35 U.S.C. 154(b) by 2457 days.

(21) Appl. No.: 12/438,383

(22) PCT Filed: Aug. 24, 2007

(86) PCT No.: PCT/US2007/018793
§ 371 (c)(1),
(2), (4) Date: Jun. 24, 2010

(87) PCT Pub. No.: WO2008/024499
PCT Pub. Date: Feb. 28, 2008

(65) Prior Publication Data
US 2010/0267573 A1    Oct. 21, 2010

Related U.S. Application Data (60) Provisional application No. 60/823,581, filed on Aug. 25, 2006.

(51) Int. Cl.
*C12Q 1/68*    (2006.01)

(52) U.S. Cl.
CPC ......... *C12Q 1/6804* (2013.01); *C12Q 1/6809* (2013.01)

(58) Field of Classification Search
USPC .......... 435/6, 91.1, 91.31, 6.1, 6.11, 91, 1.1; 536/23.1, 24.3, 24.5; 935/77, 78
See application file for complete search history.

(56) References Cited

U.S. PATENT DOCUMENTS

| | | | |
|---|---|---|---|
| 6,503,713 B1 | 1/2003 | Rana | |
| 6,635,422 B2 | 10/2003 | Keene et al. | |
| 2009/0053718 A1* | 2/2009 | Naguibneva et al. | 435/6 |

FOREIGN PATENT DOCUMENTS

WO    WO 2004/057032 A1    7/2004

OTHER PUBLICATIONS

Schwarz et al., Genes & Dev., vol. 16, pp. 1025-1031 (2002).*
Penalva et al., Methods in Molecular Biology, vol. 257, pp. 125-134 (2004).*
Keene, J.D., Proc. Nat'l. Acad. Sci., vol. 98, No. 13, pp. 7018-7024 (2001).*
Tenenbaum SA et al. Ribonomics: identifying mRNA subsets in mRNP complexes using antibodies to RNA-binding proteins and genomic arrays. Methods. 2002; 26(2): 191-198.
Tenenbaum SA et al. Genome-wide regulatory analysis using en masse nuclear run-ons and ribonomic profiling with autoimmune sera. Gene. 2003; 317: 79-87.
Penalva Lof et al. Gene expression analysis of messenger RNP complexes. Methods in Molecular Biology. Jan. 1, 2004; 257: 125-134.
Keene JD et al. RIP-chip: the isolation and identification of mRNAs, microRNAs and protein components of ribonucleoprotein complexes from cell extracts. Nature Protocols. 2006; 1(1): 302-307.
Kim VN and Nam J-W. Genomics of microRNA. Trends in Genetics. Mar. 1, 2006; 22(3): 165-173.
Supplementary European Search Report, EP 07 83 7349, Mar. 26, 2010.
Brennan CM and Steitz JA. Hur and mRNA stability. SMLS, Cellular and Molecular Life Sciences. 2001; 58: 266-277.
Keene JD. Ribonucleoprotein infrastructure regulating the flow of genetic information between the genome and the proteome. Proceedings of the National Academy of Sciences. Jun. 19, 2001; 98(13): 7018-7024.
Thomas PD et al. Panther: a library of protein families and subfamilies indexed by function. Genome Research. 2003; 13: 2129-2141.
Weiler J et al. Anti-miRNA oligonucleotides (AMOs): ammunition to target miRNAs implicated in human disease? Gene Therapy. 2006; 13: 496-502.
International Search Report and Written Opinion, PCT/US08/18793, mailed Nov. 3, 2008.
Lewis BP et al. Conserved seed pairing, often flanked by adenosines, indicates that thousands of human genes are MicroRNA targets. Cell. Jan. 14, 2005; 120: 15-20.

* cited by examiner

*Primary Examiner* — Jane Zara
(74) *Attorney, Agent, or Firm* — Myers Bigel, P.A.

(57) ABSTRACT

A method of generating a gene expression profile of non-coding regulatory RNA (ncRNA; e.g. a microRNA) in a cell in vivo, is carried out by: (a) partitioning from a cell at least one mRNA-protein (RNP) complex, the RNP complex comprising: (i) an RNA binding protein (RNABP) or RNA associated protein, (ii) at least one mRNA bound to or associated with said protein, and (iii) at least one ncRNA bound to or associated with said protein, and then (b) identifying at least one ncRNA in-at least one RNP complex, thereby to produce a gene expression profile comprising the identity of an ncRNA in an RNP complex.

15 Claims, 1 Drawing Sheet

METHODS FOR IN VIVO IDENTIFICATION OF ENDOGENOUS MRNA TARGETS OF MICRORNAS

RELATED APPLICATIONS

This application is a national phase application of PCT Application PCT/US2007/018793, filed Aug. 24, 2007, and published in English on Feb. 28, 2008, as International Publication No. WO 2008/024499, and which claims the benefit under 35 U.S.C. §119(e) of U.S. Provisional Patent Application Ser. No. 60/823,581, filed Aug. 25, 2006, the disclosure of each of which is incorporated herein by reference in its entirety.

GOVERNMENT FUNDING

This invention was made with government support under grant numbers CA79907 from the NCI. The US Government has certain rights to this invention.

FIELD OF THE INVENTION

The present invention concerns methods of identifying microRNAs and the corresponding mRNA targets thereof.

BACKGROUND OF THE INVENTION

MicroRNAs (miRNAs), together with RNA binding proteins (RNABPs), constitute the primary regulators of eukaryotic posttranscriptional gene expression and function in a broad range of cellular processes. miRNAs are a large family of small noncoding RNAs (ncRNAs) that repress gene expression by affecting the stability or translation of target messenger RNAs (mRNAs) (1-3). The current understanding of global miRNA targeting of mRNAs is based upon computational predictions of complementary sequence elements that are refined by considering evolutionary homologies across multiple species (4). While these algorithms predict hundreds of potential mRNA targets per miRNA, it is not certain that each miRNA gains functional access to these target mRNAs in the cell under a given set of conditions. Indeed, recent evidence suggests that RNABPs can influence the regulatory fates of mRNAs targeted by miRNAs in a condition-dependent manner (5, 6).

RNABPs, among the largest protein families encoded in eukaryotic genomes, can regulate gene expression at multiple posttranscriptional levels (7, 8). Like miRNAs, RNABPs also function through binding specific RNA sequence motifs frequently contained within untranslated regions (UTRs) of target mRNAs. When occurring in the cytoplasmic compartment, these interactions may determine mRNA localization, stability and/or translational activation (9). It is becoming increasingly evident that the posttranscriptional infrastructure is highly organized and utilizes multiple cis-trans interactions to combinatorially regulate higher order gene expression (7, 10). Global exploration of the in vivo composition and organization of this posttranscriptional infrastructure has only recently begun. A number of studies have identified RNABPs associated with mRNA subsets that have similar metabolic fates or encode functionally related proteins (7). Several predicted functional interactions between miRNAs and mRNAs have been confirmed using reporter systems, while a number of primarily bioinformatics approaches have predicted the global targeting of a substantial proportion of all cellular mRNAs by miRNAs (2, 4; 11). While miRNAs are expected to act combinatorially on their mRNA targets, the composition and organization of endogenous miRNAs, mRNAs and RNABPs within messenger ribonucleoprotein (mRNP) complexes are poorly understood.

SUMMARY OF THE INVENTION

A first aspect of the invention is a method of generating a gene expression profile of noncoding regulatory RNA (ncRNA) in a cell in vivo, comprising the steps of:
  (a) partitioning from a cell at least one mRNA-protein (RNP or mRNP) complex, said RNP complex comprising: (i) an RNA binding protein (RNABP) or RNA associated protein, (ii) at least one mRNA bound to or associated with said protein, and (iii) at least one ncRNA bound to or associated with said protein, and then
  (b) identifying at least one ncRNA in at least one mRNP complex, thereby to produce a gene expression profile comprising the identity of an ncRNA in an RNP complex.

In some embodiments the ncRNA is a microRNA.

In some embodiments, the invention provides a method of identifying and/or confirming mRNA target(s) of one or more microRNAs. Such a method comprises:
  (a) partitioning from a biological sample at least one RNP complex, said complex containing a subset of mRNAs associated with the RNP complex(es), and
  (b) identifying a subset of microRNA associated with the RNP complex(es), thereby determining the association between a microRNA and an mRNA target. In some embodiment, the step of partitioning comprising capturing the RNP complex(es) on a solid support. In other embodiments, the method may further comprise the step of assaying activity of at least one of the identified miRNA with respect to one or more of the identified mRNAs. In further embodiments, the method may comprise the step of predicting an mRNA target of a microRNA using in silico methods (e.g., using the TargetScanS algorithm) and validating the in silico results experimentally as described above.

A subset of cellular mRNAs is a plurality of mRNAs that includes less than, all mRNAs in the biological sample. In some embodiments, such a subset is represented by less than 75%, 70%, 60%, 50%, 40%, 30%, 25%, 20%, 15%, 10%, 5%, 2%, 1% or less of all mRNAs. A subset of microRNAs is a plurality of microRNAs that includes less than all microRNAs in the biological sample. In some embodiments, such a subset is represented by less than 75%, 70%, 60%, 50%, 40%, 30%, 25%, 20%, 15%, 10%, 5%, 2%, 1% or less of all microRNAs. A subset of mRNAs comprises at least 2 but may comprise 3, 4, 5, 10, 15, 20 or more mRNAs. Likewise, a subset of microRNAs comprises at least 2 but may comprise 3, 4, 5, 10, 15, 20 or more microRNAs. The subsets of mRNAs and microRNA may be identified in the methods of the invention, for example, by using a nucleic acid array, e.g., a microarray (e.g., cDNA array).

In some embodiments, the step of partitioning may comprise contacting an mRNP complex with (i) an antibody that specifically binds at least one component of the mRNP complex or (ii) an ectopically expressed epitope-tagged RNA-binding protein or an RNA-associated protein. In some embodiments, the component of the mRNP complex to which the antibody binds to an RNA-binding protein or an RNA-associated protein present in the mRNP complex. In some embodiments, such an RNA-binding protein is a native or tagged Hu protein (e.g., HuR) or poly(A)-binding protein (PABP). In some embodiments, the identified subset of the microRNAs includes an miRNA selected from the group consisting of miR-181a, miR-181b, miR-181c, miR-103, miR-107m miR-29c, miR-17-5p, miR-106a, miR-19b, miR-16, let-7a, let-7c, let-7d, and let-7f.

In some embodiments the step of partitioning may comprise: contacting a biological sample comprising said RNP complex from the cell with at least one ligand that specifically binds at least one component of the RNP complex; separating the RNP complex by binding the ligand with an antibody specific for the ligand, wherein the antibody is attached to a solid support; and collecting the RNP complex by removing the RNP complex from the solid support.

In some embodiments the mRNA in said RNP complex is predetermined; in some embodiments the method further comprises the step of: (c) identifying the mRNA in the mRNP complex, thereby to produce a gene expression profile further comprising the identity of the mRNA associated with said miRNA.

Any suitable cell or cells can be used to carry out the present invention, including but not limited to plant, animal, bacterial, yeast, and protozoal cell.

In some embodiments the partitioning step comprises partitioning a plurality of RNP complexes; the identifying step comprises identifying a plurality of ncRNAs associated with the plurality of RNP complexes; and the method further comprises: (c) identifying a plurality of mRNAs associated with said plurality of RNP complexes; thereby to produce a gene expression profile further comprising the identity of a subset of ncRNAs associated with a subset of mRNAs.

The present invention is explained in greater detail in the drawings herein and the specification set forth below.

BRIEF DESCRIPTION OF THE DRAWINGS

FIG. 2. Combinatorial posttranscriptional regulation mediated by RNA binding proteins and miRNAs. Depiction of gene expression networks localized to the nucleus (N) and cytoplasm. The nuclear networks involve DNA binding transcription factors, while the cytoplasmic networks involve RNABPs and miRNAs. In the nucleus, multiple promoter elements can be regulated by transcription factors. Posttranscriptional regulation primarily occurs through interaction of RNA binding factors with 5' and 3' untranslated regions (UTRs) of mRNAs. As shown, an mRNA subset regulated by a given RNABP can be further subdivided into discrete mRNA subpopulations that are also regulated in a combinatorial manner by miRNAs. The coordinated outcome depicted here applies to functional relationships among the encoded proteins or to the fates of the associated mRNAs (stability/translational state).

The present invention is explained in greater detail in the non-limiting specification and examples set forth below. The disclosures of all United States patent references cited herein are to be incorporated by reference herein in their entirety.

DETAILED DESCRIPTION

The present invention will now be described more fully with reference to the accompanying drawings and specification, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only, and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

"Messenger RNA" or "mRNA" as used herein has its ordinary meaning in the art, and generally refers to an RNA transcribed from DNA that carries encoded information to a site of protein synthesis from that mRNA by translation. mRNA as used herein may be unprocessed (pre-mRNA) or processed and hence the term is to include both. mRNA as used herein may be from any suitable source, typically vertebrate and preferably mammalian (e.g. human, dog, cat, monkey, chimpanzee, mouse, rat, rabbit, etc.).

"Noncoding regulatory RNA" or "ncRNA" as used herein has its ordinary meaning in the art. Examples include but are not limited to piRNAs, microRNAs, ribosomal RNA (rRNA), small interfering RNA (siRNA), small nuclear RNA (snRNA), small non-mRNA (snmRNA), small nucleolar RNA (snoRNA), small temporal RNA (stRNA) and other RNAs that interact with mRNAs to regulate the function thereof. See, e.g., PCT Application Publication No. WO 2005/102298.

"MicroRNA" or "miRNA" as used herein has its ordinary meaning in the art. Typically, a miRNA is a RNA molecule derived from genomic loci processed from transcripts that can form local RNA precursor miRNA structures. The mature miRNA usually has 20, 21, 22, 23, or 24 nucleotides, although in some cases, other numbers of nucleotides may be present, for example, between 18 and 26 nucleotides, miRNAs are often detectable on Northern blots. The miRNA has the potential to pair to flanking genomic sequences, placing the mature miRNA within an imperfect RNA duplex which may be needed for its processing from a longer precursor transcript. In animals, this processing may occur through the action of Drosha and Dicer endonucleases, which excise a miRNA duplex from the hairpin portion of the longer primary transcript. The miRNA duplex comprises the miRNA and a similar-sized segment, known as the miRNA* (miRNA star), from the other arm of the stem-loop. The miRNA is the strand that enters the silencing complex, whereas the miRNA* degrades. In addition, miRNAs are typically derived from a segment of the genome that is distinct from predicted protein-coding regions. See, e.g., US Patent Application Publication No. 20060185027. miRNA as used herein may be from any suitable source, typically vertebrate and preferably mammalian (e.g. human, dog, cat, monkey, chimpanzee, mouse, rat, rabbit, etc.)

"mRNA binding protein" or "RNABP", along with RNA associated proteins, as used herein have their ordinary meaning in the art, and includes global RNABPs (those that bind to nearly all mRNAs without distinguishing unique sequences), group-specific RNABPs (those that associate with subsets of the global mRNA population), and type-specific RNABPs (those that recognize a highly unique mRNA sequence, in some cases present in only one mRNA, with high specificity). See, e.g., J. Keene et al., *Proc. Natl. Acad. Sci. USA* 98, 7018, 7021 (2001). Examples include but are not limited to the ELAV/Hu family (e.g. HuR/Hul) eIF-4E, poly(A) binding proteins, the PUMILIO family (e.g., Pum1), etc. Additional examples are given in Keene et al., U.S. Pat. No. 6,635,422, at Table 1 therein, as follows:

TABLE 1

RNA Binding and RNA Associated Proteins

| | | |
|---|---|---|
| SLBP | DAN | TTP |
| HeI-N1 | HeI-N2 | eIF-4A |
| eIF-4B | eIF-4G | eIF-4E |
| eIF-5 | eIF-4EBP | MNK1 |
| PABP | p62 | KOC |
| p90 | La | Sm |
| Ro | U1-70K | AUF-1 |
| RNAse-L | GAPDH | GRSF |
| Ribosomal Po, P1, P2/L32 | PM-Scl | FMR |
| Stauffen | Crab 95 | TIA-1 |
| Upf1 | RNA BP1 | RNA BP2 |
| RNA BP3 | CstF-50 | NOVA-1 |
| NOVA-2 | CPEBP | GRBP |
| SXL | SC35 | U2AF |
| ASF/SF2 | ETR-1 | IMP-1 |
| IMP-2 | IMP-3 | ZBP |
| LRBP-1 | Barb | PTB |
| uPAmRNA BP | BARB1 | BARB2 |
| GIFASBP | CYP mRNA BP | IRE-BP |
| p50 | RHA | FN mRNA BP |
| AUF-1 | GA mRNA BP | Vigillin |
| ERBP | CRD-BP | HuA |
| HuB | HuC | HuD |
| hnRNP A | hnRNP B | hnRNP C |
| hnRNP D | hnRNP E | hnRNP F |
| hnRNP G | hnRNP H | hnRNP K |
| hnRNP L | U2AF | |

RNABPs miRNAs, and mRNAs as used herein may be from any suitable source, including bacteria, protozoa, plants and animals. Plants may be vascular plants such as monocots and dicots, with particular examples including but not limited to corn or maize, wheat, soybean, canola, tomato, etc. Animals are typically vertebrates and preferably mammals, with particular examples including but not limited to human, dog, cat, monkey, chimpanzee, mouse, rat, rabbit, etc. In particular embodiments of the invention the RNABP, miRNA, and mRNA may all be from the same cell or tissue from the same species of origin in native (non-transgenic) form.

A "subset" of mRNA, ncRNA, miRNA has its ordinary meaning in the art and is a plurality thereof, typically in an RNP complex. In other words, subsets are defined by their ability to bind within or to a particular RNP complex or subset of RNP complexes. The subset will preferably be a quantitative or qualitative fraction of the total population thereof of the cell. Furthermore, subsets within subsets of mRNAs, ncRNAs, or miRNAs may be identified using the invention. See, e.g., U.S. Pat. No. 6,635,422.

"RNA interference" or "RNAi" as used herein refers to post-transcriptional process for attenuating gene expression in which a natural (e.g., a miRNA) or artificial (e.g., an exogeneously administered double stranded RNA) interferes with the translation of a target or corresponding mRNA, e.g., by hybridization to the mRNA in a manner that interferes with normal translation thereof.

The present invention can be carried out utilizing techniques described in part in U.S. Pat. No. 6,635,422 to Keene et al., or variations thereof that will be apparent to those skilled in the art, with the provision where necessary of additional selection and identification steps for ncRNAs such as miRNAs (which can be carried out in essentially the same manner as the selection and identification of mRNAs, typically with different probe sets or microarray chips optimized for the selection and identification of the ncRNAs such as miRNAs.

Except as otherwise indicated, standard methods may be used for the production of cloned genes, expression cassettes, vectors, and transformed cells and plants according to the present invention. Such methods are known to those skilled in the art. See e.g., J. Sambrook et al., Molecular Cloning: A Laboratory Manual Second Edition (Cold Spring Harbor Laboratory, Cold Spring Harbor, N.Y., 1989); F. M. Ausubel et al., Current Protocols In Molecular Biology (Green Publishing Associates, Inc. and Wiley-Interscience, New York, 1991).

Nucleotides and amino acids are represented herein in the manner recommended by the IUPAC-IUB Biochemical Nomenclature Commission, or (for amino acids) by three letter code, in accordance with 37 C.F.R. .sctn.1.822 and established usage. See, e.g., Patentin User Manual, 99-102 (November 1990) (U.S. Patent and Trademark Office).

The terms "nucleic acid" or "nucleic acid sequence" may also be used in reference to genes, cDNA, and mRNA encoded by a gene. The term "gene" is used broadly to refer to any segment of DNA associated with a biological function. Thus, genes include coding sequences and/or the regulatory sequences required for their expression. Genes also include non-expressed DNA segments that, for example, form recognition sequences for other proteins. Genes can be obtained from a variety of sources, including cloning from a source of interest or synthesizing from known or predicted sequence information.

As used herein, a nucleic acid molecule may be RNA (the term "RNA" encompassing all ribonucleic acids, including but not limited to ncRNA, pre-mRNA, mRNA, rRNA, hnRNA, snRNA and tRNA); DNA; peptide nucleic acid (PNA, as described in, e.g., U.S. Pat. No. 5,539,082 to Nielsen et al., and U.S. Pat. No. 5,821,060 to Arlinghaus et al.); and the analogs and modified forms thereof. Nucleic acid molecules of the present invention may be linear or circular, an entire gene or a fragment thereof, full-length or fragmented/digested, "chimeric" in the sense of comprising more than one kind of nucleic acid, and may be single-stranded or double-stranded. Nucleic acid from any source may be used in the present invention; that is, nucleic acids of the present invention include but are not limited to genomic nucleic acid, synthetic nucleic acid, nucleic acid obtained from a plasmid, cDNA, recombinant nucleic acid, and nucleic acid that has been modified by known chemical methods, as further described herein. Nucleic acids may also be products of in vitro selection experiments (also called aptamers) and other nucleic acid molecules useful for their ability to bind or be bound by other ligands. See D. Kenan, TIBS 19, 57-64 (1994); L. Gold, et al., Annu. Rev. Biochem. 64, 763-798 (1995); S. E. Osborne and A. D. Ellington, Chem. Rev. 97, 349-370 (1997).

As summarized above, the present invention relates to in vivo methods for partitioning RNP complexes from a cell. mRNP complexes of the present invention is preferably from a biological sample, such as a tissue sample, whole tissue, a whole organ (e.g., an entire brain, liver, kidney, etc.), bodily fluid sample, cell culture, cell lysate, cell extract or the like.

In a preferred embodiment, the biological sample comprises or is obtained from a population of cells. By a "population of cells" herein is meant at least two cells, with at least about $10^3$ being preferred, at least about $10^6$ being particularly preferred, and at least about $10^8$ to $10^9$ being especially preferred. The population or sample can contain a mixture of different cell types from either primary or secondary cultures, or from a complex tissue such as a tumor, or may alternatively contain only a single cell type. In a preferred embodiment, cells that are proliferating are used. Alternatively, non-proliferating cells may be used.

As summarized above, one aspect of the invention is an in vivo method of partitioning endogenous cellular mRNA-binding protein (mRNP) complexes. "Endogenous" is used herein to mean that the mRNP complex forms in a cell (i.e., in vivo or in situ). The mRNP complex may form in the cell naturally, i.e., the components of the mRNP complex naturally occur in the cell and form the mRNP complex. Alternatively, the mRNP complex forms in a cell, even though one or more components of the complex is introduced into the cell by, e.g., infection or transformation. For example, an mRNP complex endogenously forms in a cell when a RNA-binding protein that is a component of the mRNP complex is ectopically expressed in the cell by (for example) transforming the cell or infecting the cell with an expression vector that carries nucleic acid encoding the protein, and a mRNP complex in which the protein binds is formed.

The method, in one embodiment, comprises contacting a biological sample that comprises at least one mRNP complex with a ligand that specifically binds a component of the mRNP complex. The component of the mRNP complex may be a RNA binding protein, a RNA-associated protein, a nucleic acid associated with the mRNP complex including the mRNA itself, ncRNAs, or another molecule or compound (e.g., carbohydrate, lipid, vitamin, etc.) that associates with the mRNP complex. A component "associates" with a mRNP complex if it binds or otherwise attaches to the mRNP complex with a Kd of about $10^6$ to about $10^9$. In a preferred embodiment, the component associates with the complex with a Kd of about $10^7$ to about $10^9$. In a more preferred embodiment, the component associates with the complex with a Kd of about $10^8$ to about $10^9$.

The ligand may be any molecule that specifically binds the component of the mRNP complex. For example, the ligand may be an antibody that specifically binds the component, a nucleic acid that binds the component (e.g., an antisense molecule, a RNA molecule that binds the component), or any other compound or molecule that specifically binds the component of the complex. In certain embodiments, the ligand may be obtained by using the serum of a subject (i.e., a human or animal subject) that has a disorder known to be associated with the production of mRNP-complex specific antibodies or proteins. Examples of these disorders include autoimmune disorders such as systemic lupus erythematosus ("lupus" or SLE) and a number of cancers. In certain embodiments, the ligand may be "tagged" with another compound or molecule in order to facilitate the separation, observation or detection of the ligand. In one embodiment of the invention, the ligand is "epitope tagged," as described in the art. Suitable tags are known in the art and include but are not limited to biotin, the MS2 protein binding site sequence, the U1snRNA 70 k binding site sequence, the U1snRNA A binding site sequence, the g10 binding site sequence (commercially available from Novagen, Inc., Madison, Wis., USA), and FLAG-TAG® (Sigma Chemical, St. Louis, Mo., USA).

The mRNP complex may then be separated by binding the ligand (now bound to the mRNP complex) to a binding molecule that specifically binds the ligand. The binding molecule may bind the ligand directly (i.e., may be an antibody or protein specific for the ligand), or may bind the ligand indirectly (i.e., may be an antibody or binding partner for a tag on the ligand). Suitable binding molecules include but are not limited to protein A, protein G, streptavidin. Binding molecules may also be obtained by using the serum of a subject suffering from, for example, an autoimmune disorder or cancer. In certain embodiments, the ligand is an antibody that binds the component of the mRNP complex via the Fab region of the antibody, and the binding molecule in turn binds the Fc region of the antibody. The binding molecule will be attached to a solid support, such as a bead, well, pin, plate or column, as known in the art. Accordingly, the mRNP complex will be attached to the solid support via the ligand and binding molecule.

The mRNP complex may then be collected by removing it from the solid support (i.e., the complex is washed off the solid support under appropriate stringency conditions, using suitable solvents that may be determined by skilled artisans).

In certain embodiments of the invention, the mRNP complex may be stabilized by cross-linking prior to binding the ligand thereto. Cross-linking, as used herein, means covalently binding (e.g., covalently binding the components of the mRNP complex together). Cross-linking may be contrasted with ligand-target binding, or binding molecule-ligand binding, which is generally non-covalent binding. Cross-linking may be carried out by physical means (e.g., by heat or ultraviolet radiation), or chemical means (e.g., by contacting the complex with formaldehyde, paraformaldehyde, or other known cross-linking agents), which means are known or determinable by those skilled in the art. In other embodiments, the ligand may be cross-linked to the mRNP complex after binding the mRNP complex. In additional embodiments, the binding molecule may be cross-linked to the ligand after binding to the ligand. In yet other embodiments, the binding molecule may be cross-linked to the solid support.

The skilled artisan will appreciate the present method allows for the identification of a plurality of mRNP complexes simultaneously (e.g., "en masse"). For example, a biological sample may be contacted with a plurality of ligands specific for different mRNP complex components. A plurality of mRNP complexes from the sample will bind the various ligands. The plurality of mRNP complexes can then be separated using appropriate binding molecules, thus isolating the plurality of mRNP complexes. The mRNP complexes and the mRNAs and ncRNAs contained within the complexes may then be characterized and/or identified by methods described herein and known in the art. Alternatively, the method may be carried out on one sample numerous times, the inventive steps being performed in a sequential fashion, with each iteration of steps utilizing a different ligand.

As set forth above, a subset of mRNA and/or ncRNAs identifies a pattern-recognition profile that is characteristic of the RNA structural or functional networks in that sample. The collection of mRNA and/or ncRNA subsets for any particular cell or tissue sample constitutes a gene expression profile, and more specifically a ribonomic gene expression profile, for that cell or tissue. It will be appreciated that ribonomic expression profiles may differ from cell to cell, depending on the type of cell in the sample (e.g., what species or tissue type the cell is), the differentiation status of the cell, the viability of the cell (i.e., if the cell is infected or if it is expressing a deleterious gene, such as an oncogene, or if the cell is lacking a particular gene or not expressing a particular gene), the specific ligands used to isolate the mRNP complexes, etc. Thus, the ribonomic expression profile of a cell may be used as an identifier for the cell, enabling the artisan to compare and distinguish profiles or subprofiles of different cells. The genes identified by the RNAs present in each ribonomic pattern form distinct subsets that may be associated with a particular cell cycle, stage of differentiation, apoptosis or stress induction, viral infection, or cancer.

cDNAs may be used to identify mRNP complexes partitioned with a ligand or ligands specific for a component of the mRNP complex. cDNA microarray grids, for example, may be used to identify mRNA and ncRNA subsets en masse. Alternatively, genomic microarrays (e.g., microarrays wherein the target nucleic acids may contain introns and exons) may be used. Therefore, each gene or target nucleic acid being examined on a microarray has a precise address that can be located, and the binding can be quantitated. Microarrays in the form of siliconized chips or those based upon cDNA blots on nylon or nitrocellulose are commercially available. Glass slides can also be customized with oligonucleotides or DNAs for detection of complementary RNA sequences. In all of these cases, the hybridization platforms allow identification of the mRNAs and ncRNAs in a sample based upon the stringency of binding and washing. This has been referred to as "sequencing by hybridization." Although microarray technology is one method of analysis, it is only one way to identify and/or sequence the mRNAs and ncRNAs in the mRNA and ncRNA subset. Alternative approaches include but are not limited to differential display, phage display/analysis, SAGE or simply preparing cDNA libraries from the mRNA and ncRNA preparation and sequencing all members of the library.

Methods for DNA sequencing which are well known and generally available in the art may be used to practice any of the embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

In a preferred embodiment, amplification of the mRNA and ncRNA isolated according to the present invention, and/or the cDNA obtained from the mRNA is not carried out during the identification of the nucleic acid, and is not necessary or required by the present invention. However, the skilled artisan may choose to amplify the nucleic acid that is the subject of identification (e.g., the nucleic acid being identified via microarray analysis and/or sequencing) for convenience, as a matter of preference, and/or to comply with the specification/instructions of certain commercially available microarrays or microarray analysis systems. Thus, if desired, the nucleic acid may be amplified according to any of the numerous known nucleic acid amplification methods that are well-known in the art (e.g., PCR, RT-PCR, QC-PCR, SDA, and the like).

Methods of the present invention may be carried out in several ways, according to the needs of the practitioner and the purpose for which the invention is carried out. For example, in one embodiment, mRNA-binding protein complexes that are unique to a cell type of interest are identified. In an example of such an embodiment, an antibody that is specific for the mRNP complex can be used to immunoprecipitate the complex with its associated mRNAs and ncRNAs. The RNAs may then identified to form the ribonomic expression profile of that cell type, or alternatively may be isolated for (as an example) drug screening. The mRNA and/or ncRNA candidates for post-transcriptional regulation may be analyzed en masse, as a subset, for changes in mRNA and/or ncRNA stability during the cell cycle or developmental events. In certain embodiments, the methods may be carried out by isolating nuclei from cells undergoing developmental or cell cycle changes, performing nuclear run-off assays according to known techniques to obtain transcribing mRNAs and/or ncRNAs, and then comparing the transcribing mRNAs and/or ncRNAs with the global mRNA and/or ncRNA levels in the same cells using cDNA microarrays. These methods thus provide the ability to distinguish transcriptional from post-transcriptional effects on steady state mRNA and/or ncRNA levels en masse.

In another embodiment, cells in culture are transformed to express a RNA-binding protein (RBP) or RNA-associated protein (RAP) that will associate with particular mRNAs and ncRNAs only in a cell type of interest. DNA encoding the RBP or RAP may be carried by a recombinant vector (e.g., a plasmid, a viral vector) and transformed into the cell by known means, after which the RBP or RAP is expressed in the cell. Any RBP or RAP can be used, as described further herein. The protein may be in its native form, or it may be tagged (e.g., epitope tagged) for easy recovery from the cell. Detection of multiple RNA targets in vivo that are bound or associated with RBPs or RAPs may be carried out by using accessible epitopes, if necessary, but preferably is carried out without tags. In cases where the epitopes on the RBPs or RAPs are inaccessible or obscured, epitope tags on ectopically expressed recombinant proteins may be used. The transformed cell may be mixed with other cell types or may be implanted in an animal or human subject. A ligand (e.g., an antibody) that is specific for the protein can used to immunoprecipitate the protein with its associated messenger RNAs from an extract of a tissue containing the transformed cell. The mRNA and ncRNA complexes and its associated RNAs may then identified to form the expression profile of that cell type or is otherwise analyzed (e.g., for drug development).

In still another embodiment, a specific cell type in an animal is engineered with one or more cell-type specific gene promoters to express a RBP or RAP in the cell type of interest. As set forth above, the gene promoter and the RBP or RAP may be carried on one or more vectors and transformed into the cell, where the RBP or RAP is expressed. In one embodiment, a ligand (e.g., an antibody) that is specific for this protein can used to immunoprecipitate the protein with its attached or associated mRNAs and ncRNAs from an extract of a tissue containing the cell type of interest. The RNAs are then identified to form the expression profile of that cell type or isolated, e.g., for drug development.

RNA binding proteins (RBPs) and RNA-associated proteins (RAPs) useful in the practice of the present invention are known in the art, or may alternatively be identified and discovered by methods described herein. RNA binding proteins are now known to be involved in the control of a variety of cellular regulatory and developmental processes, such as RNA processing and compartmentalization, RNA stabilization, mRNA translation and viral gene expression. RNA binding proteins include poly A-binding protein ("PABP," which gives rise to a subset of the total mRNA population that is quantitatively different from the total mRNA population), and other general RNA binding proteins, as well as RNA-binding proteins that are attached to only one or a few messenger RNAs in a particular cell type. Other useful proteins are autoantibodies reactive with RNA and RNA-binding proteins.

Examples of useful RNA binding proteins and RNA associated proteins are described above and include the four ELAV/Hu mammalian homologues of the Drosophila ELAV RNA-binding protein (Good (1995) Proc. Natl. Acad. Sci. USA 92, 4557-4561; Antic and Keene, supra. HuA (HuR) is ubiquitously expressed while HuB, HuC and HuD (and their respective alternatively-spliced isoforms) are predominantly found in neuronal tissue, but can also be expressed as tumor cell-specific antigens in some small cell carcinomas, neuroblastomas, and medulloblastomas (reviewed in Keene (1999) Proc. Natl. Acad. Sci. USA 96, 5-7). All Hu proteins contain three RNA-recognition motifs (RRMs), which confer their binding specificity for AREs (Antic and Keene, supra; Kenan et al. (1991) Trends Biochem. Sci. 16, 214-220; Burd and Dreyfuss (1994) Science 265, 615-621). The evidence for ARE binding by Hu proteins began with the identification of an AU-rich binding consensus sequence from a randomized combinatorial RNA library that was screened with recombinant HuB (Levine et al. (1993) Mol. Cell Biol. 13, 3494-3504; Gao et al. (1994) Proc. Natl. Acad. Sci. USA 91, 11207-11211). These and other studies demonstrated that Hu proteins bind in vitro to several ARE-containing ERG mRNAs including c-myc, c-fos, GM-CSF and GAP-43 (Levine et al. (1993) Mol. Cell Biol. 13, 3494-3504; Gao et al. (1994) Proc. Natl. Acad. Sci. USA 91, 11207-11211; King et al. (1994) J. Neurosci. 14, 1943-1952; Liu et al. (1995) Neurology 45, 544-550; Ma et al (1996) J. Biol. Chem. 271, 8144-8151; Abe et al. (1996) Nucleic Acids Res. 24, 2011-2016; Chung et al. (1997) J. Biol. Chem. 272, 6593-6598; Fan and Steitz (1998) EMBO J. 17, 3448-3460; Antic et al. (1999) Genes Dev. 13, 449-461).

The binding of Hu proteins to ARE-containing mRNAs can result in the stabilization and increased translatability of the mRNA transcripts (Jain et al. (1997) Mol. Cell Biol. 17, 954-962; Levy et al. (1998) J. Biol. Chem. 273, 6417-6423; Fan and Steitz (1998) EMBO J. 17, 3448-3460; Peng et al. (1998) EMBO J. 17, 3461-3470). The neuron-specific Hu proteins are one of the earliest neuronal markers produced in teratocarcinoma cells following retinoic acid (RA)-treatment to induce neuronal differentiation (Antic et al., supra; Gao and Keene (1996) J. Cell Sci. 109, 579-589).

In one embodiment, the ligand used to carry out the invention is a RNA binding protein selected from the RNA Recognition Motif (RRM) family of cellular proteins involved in pre-messenger RNA processing. One example of such a protein is the U1A snRNP protein. More than 200 members of the RRM superfamily have been reported to date, the majority of which are ubiquitously expressed and conserved in phylogeny (Query et al, Cell (1989) 57: 89-101; Kenan et al, Trends Biochem. Sci. (1991)16: 214-220). Most are known to have binding specificity for polyadenylate mRNA or small nuclear ribonucleic acids (e.g. U1, U2, etc.) transfer RNAs, 5S or 7S RNAs. They include but are not limited to hnRNP proteins (A, B, C, D, E, F, G, H, I, K, L), RRM proteins CArG, DT-7, PTB, K1, K2, K3, HuD, HUC, rbp9, eIF4B, sxl, tra-2, AUBF, AUF, 32 KD protein, ASF/SF2, U2AF, SC35, and other hnRNP proteins. Tissue-specific members of the RRM family are less common, including IMP, Bruno, AZP-RRMI, X16 which is expressed in pre-B cells, Bj6 which is a puff-specific Drosophila protein and ELAV/Hu, which are neuron specific.

RNA-binding and RNA-associated proteins useful in the practice of the present invention include but are not limited to those described above.

Antibodies that specifically bind mRNP complexes are known and described in, for example, U.S. Pat. No. 6,635,422 to Keene et al.

The present invention can be used to identify ncRNAs such as miRNAs that bind to, or interact with in an RNP, an mRNA encoding for a protein with which progression of a disease is associated (protein of interest). Such an mRNA may be predetermined, or identified from a subpopulation, subset of mRNAs generated by the methods of the present invention (e.g., where a cell known to express the protein of interest is utilized in carrying out the method). Examples of mRNAs encoding such proteins include but are not limited to those described in U.S. Pat. No. 6,503,713 to Rana at section 5.1 therein. Specific examples include but are not limited to mRNAs that encode proteins such as amyloid protein, amyloid precursor protein, angiostatin, endostatin, METH-1, METH-2, Factor IX, Factor VIII, collagen, cyclin dependent kinase, cyclin D1, cyclin E, WAF1, cdk4 inhibitor, MTS1, cystic fibrosis transmembrane conductance regulator gene, IL-1, IL-2, IL-3, IL-4, IL-5, IL-6, IL-7, IL-8, IL-9, IL-10, IL-11, IL-12, IL-13, IL-14, IL-15, IL-16, IL-17, erythropoietin, G-CSF, GM-CSF, M-CSF, SCF, thrombopoietin, BNDF, BMP, GGRP, EGF, FGF, GDNF, GGF, HGF, IGF-1, IGF-2, KGF, myotrophin, NGF, OSM, PDGF, somatotrophin, TGF-.beta., TGF-alpha, VEGF, interferon, TNF-alpha, TNF-beta, cathepsin K, cytochrome p-450, farnesyl transferase, glutathione-s transferase, heparanase, HMG CoA synthetase, n-acetyltransferase, phenylalanine hydroxylase, phosphodiesterase, ras carboxyl-terminal protease, telomerase, TNF converting enzyme, E-cadherin, N-cadherin, selectin, CD40, 5-alpha reductase, atrial natriuretic factor, calcitonin, corticotrophin releasing factor, glucagon, gonadotropin, gonadotropin releasing hormone, growth hormone, growth hormone releasing factor, somatotropin, insulin, leptin, luteinizing hormone, luteinizing hormone releasing hormone, parathyroid hormone, thyroid hormone, thyroid stimulating hormone, antibodies, CTLA4, hemagglutinin, MHC proteins, VLA-4, kallikrein-kininogen-kinin system, CD4, sis, hst, ras, abl, mos, myc, fos, jun, H-ras, ki-ras, c-fms, bcl-2, L-myc, c-myc, gip, gsp, HER-2, bombesin receptor, estrogen receptor, GABA receptor, EGFR, PDGFR, FGFR, NGFR, GTP-binding regulatory proteins, interleukin receptors, ion channel receptors, leukotriene receptor antagonists, lipoprotein receptors, opioid pain receptors, substance P receptors, retinoic acid and retinoid receptors, steroid receptors, T-cell receptors, thyroid hormone receptors, TNF receptors, tissue plasminogen activator; transmembrane receptors, calcium pump, proton pump, Na/Ca exchanger, MRP 1, MRP2, P170, LRP, cMOAT, transferrin, APC, brca1, brca2, DCC, MCC, MTS1, NF1, NF2, nm23, p53 and Rb. See, e.g., U.S. Pat. No. 6,503,713. Additional examples are given in US Patent Application No. 2003/0073610, at Table 1 therein, and include but are not limited to mRNAs that encode proteins involved in aberant protein deposition, such as: alpha-synuclein (Parkinson's Disease); Amyloid-beta (Alzheimer's Disease) Tau (Alzheimer's Disease), PrP (Prion Diseases); huntingtin (Huntington's Disease); Ataxin-1 (Spinocerebellar ataxia-1) Ataxin-2 (Spinocerebellar ataxia-2); Ataxin-3 (Spinocerebellar ataxia-3); Calcium channel (Spinocerebellar ataxia-6); Ataxin-7 (Spinocerebellar ataxia-7); Androgen receptor (Spinal and bulbar Muscular atrophy); Atrophin-1 (Dentatorubral Pallidoluysian atrophy); SOD1 (Amyotropic lateral sclerosis); Immunoglobulin light chain (Primary systemic amyloidosis); Transthyretin (Famylial amyloid polyneuropathy; Senile systemic amyloidosis); Serum amyloid A (Secondary systemic amyloidosis); Islet amyloid polypeptide (Type 2 diabetes); Insulin (Injection-localized amyloidosis); beta 2-microglobulin (Hemodialysis-related amyloidosis); Cystatin-C (Hereditary cerebral amyloid angiopathy); Gelsolin (Finnish hereditary systemic amyloidosis); and Lysozyme.

ncRNAs and miRNAs identified by the methods of the present invention are useful in native form or derivatized form as RNA interference (RNAi) active agents, such as described in U.S. Pat. No. 7,078,196; U.S. Pat. No. 6,503,713 (particularly section 5.2 therein); and US Patent Application 2004/0086884. Moreover, the molecular interactions and interaction sites as defined using this invention can provide validated targets for the development of compounds and reagents such as interfering RNAs.

ncRNAs and miRNAs identified by the present invention are useful in the production of proteins or peptides in vitro or in vivo, where it is desired to downregulate the production of one or more particular proteins or peptides (e.g., RNA interference during a growth phase of bacterial, plant, animal, or yeast cells), and then remove that downregulation during a subsequent production phase. Such applications would be useful in treating diseases such as those described herein and in the production of recombinant proteins and peptides.

In some cases it is desired to inhibit or inactivate an ncRNA or miRNA in vivo, for example where the downregulation of expression of a protein is undesired or pathological. In such cases ncRNAs and miRNAs of the invention are useful for designing anti-miRNA or anti-ncRNA oligonucleotides (AMOs) that hybridize thereto, which AMOs can be designed and synthesized in accordance with known techniques in order to regulate the expression of a given protein that is encoded by the mRNA target so defined. See, e.g., J. Weiler et al., *Anti-miRNA oligonucleotides (AMOs): ammunition to target miRNAs implicated in human disease*, Gene Therapy 13: 496-502 (2006).

ncRNAS and miRNAs (or subsets and combinations thereof) identified by the methods of the present invention, together with the RNABPs and corresponding mRNAs to which they bind or with which they are associated (or subsets thereof), are useful in providing confirming data, validating data, or training data to refine models and algorithms for identifying or generating hypothetical or proposed miRNAs from known corresponding mRNAs, such as described in US Patent Application 2006/0185027. For example, the data set forth in Table 2 below illustrates the narrowing of a class of 1013 mRNAs predicted as potential miRNA targets by a commercial algorithm to a smaller subset of 108 mRNAs, thereby speeding and facilitating the identification of miRNA targets.

The present invention is explained in greater detail in the following non-limiting Examples.

EXAMPLE 1

A Discrete Subset of microRNAs and Predicted mRNA Targets are Enriched Components of HuR mRNPs To examine the RNA and protein components of endogenous RNPs, we conducted a genome-wide analysis of miRNA and mRNA populations associated with the regulatory RNA binding protein HuR in the human Jurkat T cell line. The ubiquitously expressed mammalian HuR protein is one of four members of the ELAV/Hu family that all function primarily through association with AU-rich elements (AREs) in the 3'UTRs of target mRNAs, resulting in enhanced message stability and/or translation (12-14). Recently, HuR has also been shown to derepress the microRNA miR-122 translational repression of cationic amino acid transporter 1 (CAT-1) mRNA in a human hepatocellular carcinoma cell line subjected to stress conditions (6).

Here we report that discrete subsets of miRNAs and mRNAs are associated with HuR in human Jurkat T cells and that the mRNA subpopulation is highly enriched for computationally predicted miRNA targets that encode many growth regulatory proteins. Among the fourteen miRNAs found in the HuR mRNP are members of the mir-17-92 cluster previously implicated as an oncogene, as well as miR-16 which is reported to be associated with apoptosis, chronic lymphocytic leukemia and ARE-mediated mRNA decay (5, 15-17). This report is the first demonstration that subsets of miRNAs are components of specific RNP complexes that are also enriched for functionally related target mRNAs. As biologically derived co-subsets, these HuR RNP-associated miRNAs and mRNAs provide a greatly reduced sequence space in which to examine miRNA targeting and the outcomes of predicted miRNA:mRNA interactions in a given cellular context. We address possible combinatorial relationships between RNABPs and miRNAs, regulation of the targeted mRNA subpopulations and resultant gene expression networks. We propose that mRNAs regulated by one posttranscriptional mechanism such as RNABPs may have preferentially evolved or acquired additional posttranscriptional regulators to diversify and coordinate the outcomes of gene expression.

Figure 1:
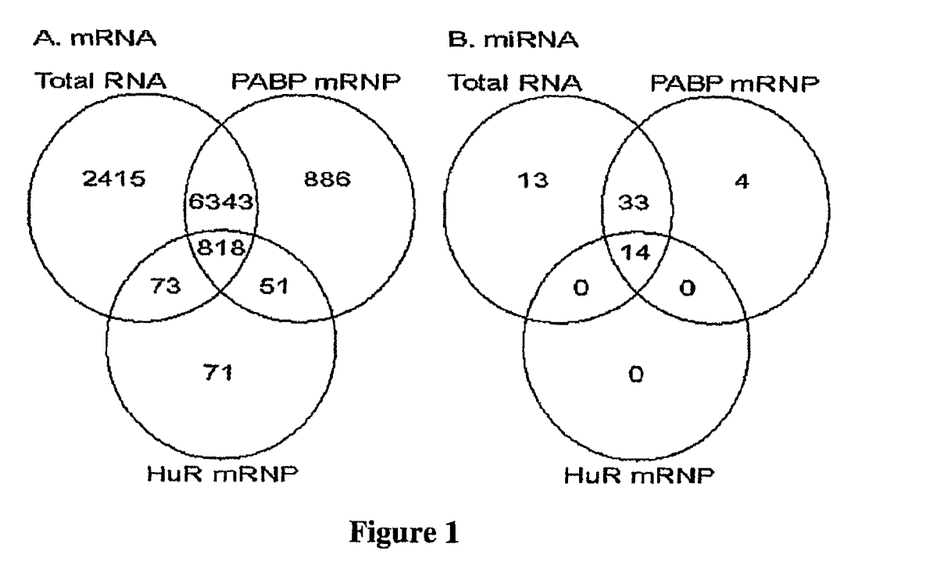
FIG. 1. HuR-associated mRNAs and miRNAs are discrete subsets of total cellular RNA. Venn diagrams representing distinct (A) messenger RNAs (mRNAs) and (B) microRNAs (miRNAs) present in total cellular RNA, the PABP mRNP and the HuR mRNP. All RNA populations were isolated as single samples from log phase Jurkat cells and subsequently divided for analysis of mRNAs and miRNAs on specific microarray platforms. Data was gathered from three biological replicates and triplicate array analyses.
Figure 2:
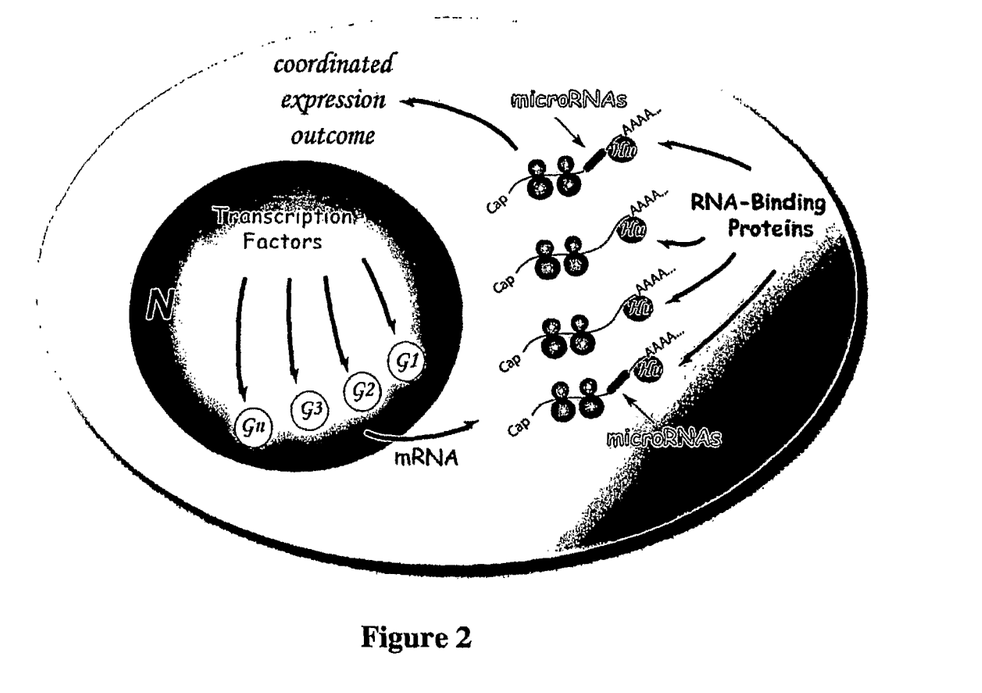

In this study, endogenous HuR and poly(A)-binding protein (PABP) mRNPs were directly isolated from Jurkat cell lysates by immunoprecipitation with specific antibodies. RNA extracted from these mRNPs, as well as from total cellular RNA, was analyzed on a commercially available mRNA microarray platform and a previously validated array platform specific for miRNAs (see Materials and Methods). The results demonstrate that HuR associates in vivo with a distinct subset of both the total cellular mRNAs and miRNAs (FIG. 1). Interestingly, HuR associates with a larger fraction of cellular miRNAs (23%) than mRNAs (10%), while PABP associates proportionally with each (85% and 84%, respectively). Two other RNABPs were also tested and did not produce these RNA subsets (data not shown). The 14 miRNAs associated with HuR are grouped into 7 miRNA families out of the approximately 62 known families based on seed sequence conservation (Table 1A) (18, 19). Several of the HuR-associated miRNAs have previously been reported to function in processes also associated with ARE-mediated RNA stability and translation in which Hu proteins are well established regulators. These include effects on cellular proliferation and apoptosis by miR-16, the miR-17 oncomir cluster (including miR17-5p and miR-19b) and the let-7 family (13, 15, 16, 20, 21). In addition, miR-16 has been implicated in TNF-α mRNA instability mediated through an ARE sequence motif that is also an expected binding site of the RNABPs tristetraprolin (TTP) and HuR (5).

To address the targeting of mRNAs by the HuR-associated miRNA subset, we utilized the TargetScanS algorithm that relies upon evolutionary conservation of miRNA seed matches to predict target mRNAs (19). The 7 HuR-associated miRNA families are predicted to target 1084 mapped mRNAs conserved in the 3'UTRs of 5 vertebrate species (see Materials and Methods). 439 of these mRNAs are expressed in Jurkat cell total RNA, while 108 are associated with HuR (Table 2). The association of these 108 mRNAs with HuR represents an exceptional enrichment of miRNA targets as determined using TargetScanS and was confirmed by a hypergeometric statistical test that yields a P value of 2.6e-16 (probability that miRNA target enrichment in the HuR mRNP occurs by chance). Additional analyses of groups of 7 miRNA family sets randomly chosen from all miRNAs (representing 62 families) also show target enrichment to mRNAs in the HuR mRNP. Interestingly, only an additional 130 mRNAs are added to the targeted subpopulation in this case (data not shown). Taken together, these data demonstrate that the discrete subpopulation of HuR-associated mRNAs is preferentially targeted by miRNAs. This is consistent with the fact that many mRNA targets of Hu family proteins encode early response gene proteins involved in cell growth and differentiation, processes also implicated in miRNA regulation (1, 2, 12, 13, 22).

Gene ontology analysis of mRNAs predicted to be targets of HuR-associated miRNAs reveals an enrichment of several functional annotation groups (Table 3). HuR-associated miRNA targets encode proteins that show statistically significant enrichment in 10 annotation groups, while those expressed globally in Jurkat total RNA are enriched in 16 categories. Interestingly, only 3 functional groups overlap between the two analyses, suggesting again that the association of predicted miRNA targets with HuR is not random and represents enrichment in distinct functional classes. The predicted mRNA targets of miRNAs found to be associated with HuR are predominantly enriched in functional categories relating to transcriptional regulation and RNA metabolism, two areas also attributed to HuR regulation (13, 23). These findings are consistent with an interconnection and potential coordination of transcriptional and posttranscriptional regulatory networks by RNABPs and miRNAs (7, 22-24).

Current understanding of the global populations of mRNAs that may be directly targeted by miRNAs relies almost entirely upon computational approaches, and these algorithms have significantly advanced functional predictions of these interactions. However, reliance upon strict evolutionary conservation in these predictions may overlook mRNA targets that are species specific. Isolation of endogenously associated miRNA:mRNA subpopulations as reported here substantially reduces the sequence space to be examined for productive interactions, many of which may depend upon cell type, growth condition or intracellular context. As an analogy, RNABPs, and RNPs in general, have been demonstrated to exhibit condition dependent association with mRNA targets (22). It is apparent that the simple presence of an RNABP and a target mRNA in a given cell is not the sole determinant of their in vivo interaction. The mechanisms underlying these dynamics are not well understood, but may include subcellular compartmentalization, posttranslational modification of components of the RNP, the presence of either protein or noncoding RNA accessory factors and competition or cooperation with other posttranscriptional mediators (13, 25). Previous reports that the RNABP TTP functions interdependently with miR-16 in ARE-mediated decay of tumor necrosis factor mRNA, and that HuR can conditionally derepress miR-122 mediated translational inhibition, also indicate the importance of cellular context in which to investigate functional interactions between posttranscriptional mediators (5, 6). The relief of miR-122 repression by HuR resulted in recruitment of the targeted mRNA to actively translating polysomes, consistent with previous studies with the neuronal HuB protein (12). Our current results support the suggestion that miRNA:mRNA interactions are maintained upon HuR binding of co-targeted transcripts (6). However, it is not known whether relief of miRNA-mediated translational inhibition is universally the result of co-targeting of mRNAs by HuR. If HuR recruitment of these mRNAs to active polysomes is a more general mechanism of miRNA derepression, and the miRNA interactions with the mRNAs are maintained, it would provide the potential for dynamic reversibility of this derepression on a more global level if cellular conditions change and the HuR association is then lost. Further studies will be required to understand how HuR and the HuR RNP-associated miRNA subset reported here influence the contextual fate of the broader co-associated mRNA populations and resultant protein expression.

The data presented here also support a corollary to the posttranscriptional RNA operon theory (7, 24). A central assertion of this model is that functionally related genes are co-regulated combinatorially at the posttranscriptional level by trans-acting factors such as RNABPs and miRNAs that recognize related regulatory sequence elements in the respective mRNAs. Our demonstration of the association of a discrete miRNA subset with a specific group of target-enriched mRNAs in the HuR mRNP supports this model. Furthermore, it suggests that RNABP-associated mRNAs may be further divided into subpopulations based upon potential regulation by other posttranscriptional mediators such as miRNAs. The added layers of combinatorial regulation are potentially vast, and may allow for extensive fine-tuning of gene expression as well as agility, while maintaining broader canalization of developmental programs (26).

HuR is the first RNABP reported to associate with a discrete subset of miRNAs, in addition to a subset of mRNAs enriched for predicted targets of miRNAs. As HuR is an established ARE binding and regulatory protein, these data are consistent with bioinformatics approaches that have been used to predict the preferential targeting by human miRNAs of mRNAs containing AU-rich 3'UTRs (27). Moreover, UTR evolution and the robustness of gene expression programs appear to have been significantly influenced by posttranscriptional regulators (7-9, 28-30). Our data suggest that the combinatorial effects of different classes of posttranscriptional factors may in fact mediate this evolutionary progression. Given that we find a subpopulation of HuR-associated mRNAs highly enriched for predicted miRNA targets in mammalian cells, we propose that many posttranscriptionally regulated mRNAs may have evolved or acquired sequence elements that enabled combinatorial regulation via multiple mechanisms. A more thorough understanding of the coordination of these RNA-RNA and RNA-protein interactions will require the elucidation of biologically defined networks involving RNABPs, miRNAs and the messenger RNAs they co-target.

REFERENCES

1. V. Ambros, *Cell* 107, 823 (2001).
2. D. P. Bartel, *Cell* 116, 281 (2004).
3. M. A. Valencia-Sanchez, J. Liu, G. J. Hannon, R. Parker, *Genes Dev* 20, 515 (2006).
4. N. Rajewsky, *Nat Genet* 38 Suppl 1, S8 (2006).
5. Q. Jing et al., *Cell* 120, 623 (2005).
6. S. N. Bhattacharyya, R. Habermacher, U. Martine, E. I. Closs, W. Filipowicz, *Cell* 125, 1111 (2006).

7. J. D. Keene, P. J. Lager, *Chromosome Res* 13, 327 (2005).
8. H. Hieronymus, P. A. Silver, *Genes Dev* 18, 2845 (2004).
9. M. J. Moore, *Science* 309, 1514 (2005).
10. D. P. Bartel, C. Z. Chen, *Nat Rev Genet* 5, 396 (2004).
11. L. P. Lim et al., *Nature* 433, 769 (2005).
12. D. Antic, N. Lu, J. D. Keene, *Genes Dev* 13, 449 (1999).
13. C. M. Brennan, J. A. Steitz, *Cell Mol Life Sci* 58, 266 (2001).
14. I. Lopez de Silanes, M. Zhan, A. Lal, X. Yang, M. Gorospe, *Proc Natl Acad Sci USA* 101, 2987 (2004).
15. L. He et al., *Nature* 435, 828 (2005).
16. A. Cimmino et al., *Proc Natl Acad Sci USA* 102, 13944 (2005).
17. K. A. O'Donnell, E. A. Wentzel, K. I. Zeller, C. V. Dang, J. T. Mendell, *Nature* 435, 839 (2005).
18. B. P. Lewis, I. H. Shih, M. W. Jones-Rhoades, D. P. Bartel, C. B. Burge, *Cell* 115, 787 (2003).
19. B. P. Lewis, C. B. Burge, D. P. Bartel, *Cell* 120, 15 (2005).
20. A. Lal, T. Kawai, X. Yang, K. Mazan-Mamczarz, M. Gorospe, *Embo J* 24, 1852 (2005).
21. S. M. Johnson et al., *Cell* 120, 635 (2005).
22. S. A. Tenenbaum, C. C. Carson, P. J. Lager, J. D. Keene, *Proc Natl Acad Sci USA* 97, 14085 (2000).
23. J. D. Keene, *Proc Natl Acad Sci USA* 98, 7018 (2001).
24. J. D. Keene, S. A. Tenenbaum, *Mol Cell* 9, 1161 (2002).
25. A. Lal et al., *Embo J* 23, 3092 (2004).
26. E. Hornstein, N. Shomron, *Nat Genet* 38 Suppl 1, S20 (2006).
27. H. Robins, W. H. Press, *Proc Natl Acad Sci USA* 102, 15557 (2005).
28. A. Stark, J. Brennecke, N. Bushati, R. B. Russell, S. M. Cohen, *Cell* 123, 1133 (2005).
29. M. Legendre, W. Ritchie, F. Lopez, D. Gautheret, *PLoS Comput Biol* 2, e43 (2006).
30. I. Rigoutsos et al., *Proc Natl Acad Sci USA* 103, 6605 (2006).

TABLE 1A

HuR associates with seven miRNA families*

| Human miRNA Family | Seed + m8 | HuR-associated miRNAs |
|---|---|---|
| miR-181 | ACAUUCA | miR-181a, miR-181b, miR-181c |
| miR-103 | GCAGCAU | miR-103, miR-107 |
| miR-29b | AGCACCA | miR-29c |
| miR-20 | AAAGUGC | miR-17-5p, miR-106a |
| miR-19 | GUGCAAA | miR-19b |
| miR-15 | AGCAGCA | miR-16 |
| let-7 | GAGGUAG | let-7a, let-7c, let-7d, let-7f |

*The 14 miRNAs associated with HuR in Jurkat cells represent 7 families based on seed sequence conservation. These 7 human miRNA families, the related seed sequence plus 1 nucleotide (utilized for predicting mRNA targets of miRNAs), and the HuR-associated miRNAs which are grouped into each microRNA family are shown.

TABLE 2

HuR associates with mRNAs enriched for predicted targets of miRNAs.*

| RNA Source | Mapped mRNAs | mRNA Targets of HuR-associated miRNAs |
|---|---|---|
| Total RNA | 7543 | 439 |
| HuR mRNP | 1013 | 108 |
| HuR mRNP as % of Total RNA | 11% | 25%[#] |

*The 7 families of miRNAs associated with HuR are predicted by the TargetScanS algorithm to target a subpopulation of mRNAs that are significantly enriched in the HuR RNP when compared to total cellular RNA. Mapped mRNA numbers represent those unique mRNAs in total cellular RNA and the HuR mRNP that were found to overlap between the array platform and the gene list utilized for TargetScanS predictions. This overlap consisted of 7543 mRNAs in total RNA and 1013 mRNAs in the HuR mRNP. P value for enrichment of predicted targets in the HuR mRNP (2.6e−16) was calculated using a hypergeometric statistical analysis (see Materials and Methods).
[#]p value = 2.6e−16 (miRNA target enrichment in HuR mRNP)

TABLE 3

Predicted mRNA targets of HuR-associated miRNAs are enriched for specific gene ontology functional categories.*

| A. miRNA targets in HuR mRNP | | B. miRNA targets in total RNA only | |
|---|---|---|---|
| GO Category | p value | GO Category | p value |
| Nucleoside, Nucleotide and Nucleic Acid Metabolism | 7.30e−06 | Nucleoside, Nucleotide and Nucleic Acid Metabolism | 1.47e−08 |
| Nucleic Acid Binding | 7.65e−04 | mRNA Transcription | 1.36e−07 |
| Other Ligase | 6.50e−03 | mRNA Transcription Regulation | 1.19e−06 |
| Other Transcription Factor | 1.04e−02 | Protein Kinase | 3.06e−05 |
| Ligase | 1.06e−02 | Protein Phosphorylation | 4.44e−05 |
| Other Protein Metabolism | 1.69e−02 | Transcription Factor | 5.48e−05 |
| Pre-mRNA Processing | 1.94e−02 | Protein Modification | 2.49e−04 |
| mRNA Splicing | 3.10e−02 | Cell Cycle | 2.57e−04 |
| mRNA Transcription | 3.12e−02 | Developmental Process | 3.25e−04 |
| Other Miscellaneous Protein Function | 4.80e−02 | Kinase | 3.57e−04 |
| | | Protein Metabolism & Modification | 2.42e−03 |
| | | Non-receptor Serine/Threonine Protein Kinase | 5.66e−03 |
| | | Transcription Cofactor | 1.75e−02 |
| | | General Vesicle Transport | 1.77e−02 |
| | | Intracellular Protein Traffic | 1.98e−02 |
| | | Other Transcription Factor | 4.32e−02 |

*Gene ontology functional category enrichment for predicted mRNA targets of HuR-associated miRNAs in (A) HuR mRNP and (B) total RNA only. Gene list comparisons were carried out using the "PANTHER" database. Enrichment p values were calculated against NCBI *Homo sapiens* gene list using the Binomial statistic with Bonferroni correction for multiple testing.

Materials and Methods

Cell Culture and Preparation of Lysates.

Human acute T cell leukemia Jurkat cells were cultured in RPMI 1640 supplemented with 10% FBS (GIBCO/BRL). Lysates were prepared essentially as described (1). Exceptions include the addition of 10% glycerol to the polysome lysis buffer and passage of cell lysate through a 27 gauge needle 10 times after resuspension of harvested cells in lysis buffer.

IP Assays and Isolation of RNA.

IP of endogenous HuR and PABP mRNP complexes were used to assess association of endogenous target mRNAs. Assays were performed essentially as described (1, 2). IPs utilized 200 µl pre-swollen and packed Protein-A Sepharose beads (Sigma) loaded with 60 µg of anti-HuR (3A2) (3), anti-PABP (4), IgG1 (BD PharMingen) or normal rabbit sera immunoglobulin. Antibody loaded beads were incubated with 5 mg (total protein) cell lysate for four hours at 4° C., washed 4 times with ice-cold NT2 buffer (50 mM Tris pH 7.4/150 mM NaCl/1 mM MgCl2/0.05% Nonidet P-40) followed by 3 washes with ice-cold NT2 supplemented with 1M Urea. Extraction of associated RNA was performed as described (1), and total RNA was isolated using the Trizol reagent (GIBCO/BRL). All RNA samples were divided into two aliquots for subsequent analysis on mRNA or miRNA arrays.

mRNA Array Analysis.

Total and RNP-associated RNA (and negative control IPs) were assayed for mRNAs on two color Operon Human Oligo Arrays (version 2.1) as described (5). Probe production used direct labeling of experimental samples (Cy 3) and Stratagene Universal Human Reference RNA (Cy 5). Results were analyzed using GeneSpring GX 7.3 (Agilent) with per spot and per chip (lowess) normalization. mRNAs were determined to be components of total RNA or specific endogenous targets of a given RNABP if present on 2 of 3 biological replicate arrays at a level of 2 fold above local background in the experimental channel as well as 10 fold above signal/noise ratio of parallel negative control IP (IgG1 or normal rabbit sera).

microRNA Array Analysis.

Total and RNP-associated RNA (and negative control IPs) were assayed for miRNAs using a custom array platform capable of detecting 156 human miRNAs essentially as described (6). Exceptions include using 10 µg/ml BSA in the labeling buffer and a reference oligonucleotide concentration of 0.05 µM for labeling. Arrays were washed once in 2×SSC/0.025% SDS at 25° C., three times in 0.8×SSC at 23° C., and twice in 0.4×SSC at 4° C. Computational analysis on each array was performed as described (6). miRNAs were determined to be components of total RNA or associated with a given RNABP if present on 2 of 3 biological replicate arrays at a level of 2 fold above local background in duplicate spots as well as 10 fold above signal/noise ratio of parallel negative control IP (IgG1 or normal rabbit sera).

microRNA Target Enrichment Analysis.

miRNA target predictions were taken from the supplementary data of Lewis et al. (7). This algorithm uses multiple alignments to identify conserved Watson/Crick hexamer matches to bases 2-7 of a miRNA, flanked by either a Watson/Crick match to position 8 of the miRNA or a conserved adenosine in position 1 of the target. We used the 12928 predictions conserved in 5-species alignments (human, mouse, rat, dog, and chicken). Lewis et al. provide these predictions as IDs of cDNAs obtained from the UCSC genome annotations which may lead to duplicate entries in the form of several cDNAs reported for one gene. To remove these duplicates, we mapped the predicted mRNA targets to unique Ensembl gene IDs as of August 2005, leaving 10182 predictions. Ensembl IDs also allowed us to match predicted target genes to the mRNA microarray probes (Table 2). We mapped targets for all 62 miRNA families to 2518 genes represented on the mRNA array platform, 1003 of which were detected as expressed in Jurkat cells. Enrichment of targeted mRNAs associated with HuR was determined by hypergeometric tests in comparison with total cellular RNA.

Gene Ontology Enrichment Analysis.

Gene lists of mRNAs predicted to be targets of HuR-associated miRNAs were compared against the complete NCBI *H. sapiens* gene list using the Panther database (8). Significant enrichment in a functional category was determined using the Binomial statistic with Bonferroni correction for multiple testing (p value <0.05).

REFERENCES

1. S. A. Tenenbaum, C. C. Carson, P. J. Lager, J. D. Keene, *Proc Natl Acad Sci USA* 97, 14085 (2000).
2. I. Lopez de Silanes, M. Zhan, A. Lal, X. Yang, M. Gorospe, *Proc Natl Acad Sci USA* 101, 2987 (2004).
3. I. E. Gallouzi et al., *Proc Natl Acad Sci USA* 97, 3073 (2000).
4. L. O. Penalva, M. D. Burdick, S. M. Lin, H. Sutterluety, J. D. Keene, *Mol Cancer* 3, 24 (2004).
5. J. A. Gollob, C. J. Sciambi, Z. Huang, H. K. Dressman, *Cancer Res* 65, 8869 (2005).
6. J. M. Thomson, J. Parker, C. M. Perou, S. M. Hammond, *Nat Methods* 1, 47 (2004).
7. B. P. Lewis, C. B. Burge, D. P. Bartel, *Cell* 120, 15 (2005).
8. H. Mi et al., *Nucleic Acids Res* 33, D284 (2005).

The foregoing is illustrative of the present invention, and is not to be construed as limiting thereof. The invention is defined by the following claims, with equivalents of the claims to be included therein.

That which is claimed is:

1. A method of identifying and/or confirming mRNA target(s) of one or more microRNAs, the method comprising:
    (a) partitioning from a biological sample at least one RNP complex, said complex containing a subset of mRNAs associated with the RNP complex(es), and
    (b) identifying a subset of microRNA associated with the RNP complex, thereby determining the association between a microRNA and an mRNA target.

2. The method of claim 1, wherein the step of partitioning comprises capturing the RNP complex(es) on a solid support.

3. The method of claim 1, further comprising assaying activity of at least one of the identified miRNA with respect to one or more of the identified mRNAs.

4. The method of claim 1, further comprising predicting an mRNA target of a microRNA in silico.

5. The method of claim 1, wherein the subset of mRNAs is represented by less than 75% of all mRNAs in the biological sample.

6. The method of claim 1, wherein the subset of mRNAs comprises at least 2 mRNAs.

7. The method of claim 1, wherein the subset of miRNAs is represented by less than 75% of all miRNAs in the biological sample.

8. The method of claim 1, wherein the subset of miRNAs comprises at least 2 miRNAs.

9. The method of claim 1, wherein the subset of miRNAs and/or the subset of the cellular miRNAs is/are identified by using a nucleic acid array.

10. The method of claim 1, wherein the step of partitioning may comprise contacting an mRNP complex with (i) an antibody that specifically binds at least one component of the mRNP complex or (ii) an ectopically expressed epitope-tagged RNA-binding protein or an RNA-associated protein.

11. The method of claim 7, wherein the RNA-binding protein is a native or tagged Hu protein or poly(A)-binding protein (PABP).

12. The method of claim 1, where the identified subset of the microRNAs includes an miRNA selected from the group consisting of miR-181a, miR-181b, miR-181c, miR-103, miR-107m miR-29c, miR-17-5p, miR-106a, miR-19b, miR-16, let-7a, let-7c, let-7d, and let-7f.

13. The method of claim 1, said RNP complex comprising: (i) an RNA binding protein (RNABP) or RNA associated protein, (h) at least one mRNA bound to or associated with said protein, and (iii) at least one microRNA bound to or associated with said protein.

14. A method of identifying and/or confirming mRNA target(s) of one or more microRNAs, the method comprising:
(a) partitioning from a biological sample at least one RNP complex, said RNP complex comprising: (i) an RNA binding protein (RNABP) or RNA associated protein, (ii) at least one mRNA bound to or associated with said protein, and (iii) at least one microRNA bound to or associated with said protein, and said complex containing a subset of mRNAs associated with the RNP complex(es), and
(b) identifying a subset of microRNA associated with the RNP complex, thereby determining the association between a microRNA and an mRNA target, wherein:
the subset of mRNAs is represented by less than 75% of all mRNAs in the biological sample; and
the subset of miRNAs is represented by less than 75% of all miRNAs in the biological sample.

15. The method of claim 14, wherein:
the subset of mRNAs comprises at least 2 mRNAs; and
the subset of miRNAs comprises at least 2 miRNAs.

* * * * *

UNITED STATES PATENT AND TRADEMARK OFFICE
CERTIFICATE OF CORRECTION

PATENT NO.       : 9,617,581 B2
APPLICATION NO.  : 12/438383
DATED            : April 11, 2017
INVENTOR(S)      : Keene et al.

Page 1 of 1

It is certified that error appears in the above-identified patent and that said Letters Patent is hereby corrected as shown below:

In the Claims

Column 21, Claim 13, Line 20: Please correct "protein, (h)" to read -- protein, (ii) --

Signed and Sealed this
Twentieth Day of February, 2018

Andrei Iancu
*Director of the United States Patent and Trademark Office*